United States Patent [19]
Lautenschläger

[11] Patent Number: 5,858,178
[45] Date of Patent: Jan. 12, 1999

[54] PROCESS AND DEVICE FOR PREPARING AND/OR EXTRACTING SAMPLES USING A VAPORIZABLE AGENT AT HIGH TEMPERATURE

[76] Inventor: Werner Lautenschläger, Waldstrasse 15, D-88299 Leutkirch, Germany

[21] Appl. No.: 704,611
[22] PCT Filed: Mar. 22, 1995
[86] PCT No.: PCT/EP95/01081
   § 371 Date: Sep. 20, 1996
   § 102(e) Date: Sep. 20, 1996
[87] PCT Pub. No.: WO95/25572
   PCT Pub. Date: Sep. 28, 1995

[30] Foreign Application Priority Data

Mar. 22, 1994 [DE] Germany .......................... 44 09 877.4
Jun. 4, 1994 [DE] Germany .......................... 44 19 648.2

[51] Int. Cl.⁶ .............................. B01D 3/00; B01D 3/10; B01D 3/42
[52] U.S. Cl. .............................. 203/73; 203/100; 159/22; 159/47.1; 159/DIG. 16; 159/DIG. 26; 202/175; 202/205; 202/206; 202/235
[58] Field of Search .................... 202/205, 206, 202/235, 175; 159/22, DIG. 16, DIG. 26, 47.1; 203/73, 100

[56] References Cited

U.S. PATENT DOCUMENTS

| | | | |
|---|---|---|---|
| 4,265,860 | 5/1981 | Jennings et al. | 422/280 |
| 4,488,935 | 12/1984 | Ruhe | 202/177 |
| 5,098,662 | 3/1992 | Killough | 422/102 |
| 5,174,864 | 12/1992 | Arbizzani et al. | 202/175 |
| 5,338,409 | 8/1994 | Heierli | 202/205 |
| 5,382,414 | 1/1995 | Lautenschlager | 422/186 |
| 5,445,714 | 8/1995 | Myers | 202/176 |
| 5,447,077 | 9/1995 | Lautenschlager | 73/863.11 |

FOREIGN PATENT DOCUMENTS

| | | |
|---|---|---|
| 4114525A1 | 8/1992 | Germany . |
| WO9322650 | 11/1993 | WIPO . |

*Primary Examiner*—Nina Bhat
*Attorney, Agent, or Firm*—Fitzpatrick, Cella, Harper & Scinto

[57] ABSTRACT

A process for preparing and/or extracting samples by heating them together with a solvent in a container under pressure, using a Soxhlet apparatus. The samples are dried by heating in a container; and the resultant vapors are drawn off to generate a vacuum in the container.

30 Claims, 4 Drawing Sheets

PROCESS AND DEVICE FOR PREPARING AND/OR EXTRACTING SAMPLES USING A VAPORIZABLE AGENT AT HIGH TEMPERATURE

This application is a national stage application filed under 371 of PCT/EP95/01081.

BACKGROUND OF THE INVENTION

1. Field of the Invention

The invention relates to an improved process and apparatus from which a sample is extracted under conditions of high temperature and high pressure.

2. Description of the Related Art

It is known that an extractor of the type known as 10 Soxhlet can be used for the multiple extraction of samples, whereby the solvent can be distilled off and the desired substance(s) can be extracted from the sample in a continuous cycle.

There are such devices in which the distillation and extraction take place at normal (ambient) pressure or at elevated pressure (high-pressure extraction).

A device of the above referred to type is familiar as a one-piece glass molded article, which consists of an upper glass flask for the samples and a lower glass flask for the solvent, and two separate external connection tubes that connect the lower and upper glass flasks together. One of the connection tubes is a vapor tube, which branches off from the lower glass flask and leads into the upper glass flask near the top thereof. The other connection tube is an overflow tube which starts from the lower part of the upper glass flask, extends upwards in it up to a certain level, and then leads down into the lower glass flask.

This known device is expensive, in relation both to its construction and to the procedures that can be carried out with it. Heating of both the solvent and the sample material is difficult, firstly because the heat from a heat source, for example a Bunsen burner, is not easy to transfer to the materials being heated, and then because glass, as a construction material, is a poor conductor of heat. As a rule, this known device is only made in relatively small sizes, so that only small extraction jobs can be carried out. A further disadvantage of the known device is that since it is made of glass, it is very sensitive and can break easily.

A high-pressure extraction device is described in USA 4 265 860 or in DE A1 4 114 525.9. In this known device the extractor is housed in a pressure-tight housing with a charging opening closed off by a cover. During operation of the device, distillation of the solvent increases the pressure in the pressure vessel, which causes the boiling point of the solvent to rise and so increases the working temperature. This substantially enhances the performance of the device, and in addition the elevated pressure favors the extraction of the samples because the solvent can penetrate better into the sample material.

In addition, in the device known from DE,A1, 4 114 525.9, two receptacles are provided in the pressure vessel, namely one solvent container made of plastic lining the inner wall of the metal pressure vessel, and inside and concentric with that, a glass sample container resting on a shoulder and fitted with an external overflow pipe connected in one piece with the sample container. The sample container is arranged a certain distance above the bottom of the solvent container, supported by a circular flange that rests against an interior shoulder of the solvent container. The solvent and sample materials are heated by microwave radiation admitted via an opening at the bottom of the pressure vessel covered by a material transparent to microwaves. When the solvent evaporates, the vapor passes upwards into the annular space between the solvent container and the sample container, and through holes in the circular flange into the vapor space over the sample container. In the area of the vapor space, the pressure vessel is surrounded by a cooling device formed by an annular water pipe in the peripheral wall of the pressure vessel and therefore in direct contact with the upright wall thereof. Over the sample container is a perforated screen over which the solvent condensed by the cooling device against the upright inner wall flows and falls into the sample container.

In WO 93 22650 devices for the vaporization or drying and extraction of samples are described in several design variants (see FIGS. 1 to 23). In these design examples, the inside of at least one container for receiving and treating the sample is connected to a suction device by means of one suction pipe, and by means of a common or two separate inlet pipes to a flushing gas supply device and/or a supply device for a reagent or solvent. During the vaporization treatment, the vapors given off when the sample is heated are continually extracted by the suction device, producing an underpressure in the container which lowers the boiling and evaporation points of the reagent, so that the sample can be treated at a lower temperature. This is especially advantageous when the sample material and/or the reagent medium must not be treated at higher temperatures, which they may not tolerate for example.

FIG. 24 of this specification shows a device for the preparation of samples under the action of heat and elevated pressure.

SUMMARY OF THE INVENTION

The object of the invention is to develop the process and the equipment further, in such a way as to enable more rational treatment of the samples.

In the process according to the invention, a sample is not only extracted under elevated pressure, but also, before and/or after its preparation and/or extraction, it is dried under reduced pressure. This achieves the desired rational and simple procedure, allowing accurate analysis of the sample and determination of its constituents, since largely accurate measurement values can be obtained and faulty measurements avoided. The device of the invention is also constructed simply and can be operated conveniently, rapidly and safely.

In both of the previously known devices, the formation of solvent vapor is prejudiced. In the first of the known devices described, the vapor must first flow through an external tube with a relatively small internal cross-15 section, and then through an external cooling zone. In the second of the known devices described, the vapor flow is impeded by the overflow pipe. Furthermore, both of the known designs are sensitive and fragile.

A further development of the invention confers the advantage that vapor flow will be improved while guaranteeing a simple structure.

In this further development, the overflow duct is integrated as a groove or channel in the body or wall of the sample container. Thus, the overflow duct is no longer in the way of the vapor flow and this also makes for a smaller, compact and robust structure, since there is no projecting pipe that could be broken or damaged.

By means of the further development, the heating of the solvent and/or the sample material is improved, and in addition, solvents can be used which do not absorb microwaves. In this further development, the solvent and/or sample material are if necessary additionally heated indirectly, considerably reducing the operation time and improving the performance.

According to another development of the invention, a simple structure inexpensive to manufacture is achieved, which guarantees safety and robustness. In this further development, the pressure vessel is at the same time the container for the solvent, whereby a further important simplification is achieved since no connection aperture need be provided and simpler and more effective coupling is guaranteed.

The further development of this invention improves the cooling or formation of condensate. In this further development, the cooling device is arranged in the area of the cover of the pressure vessel. This not only avoids any weakening of the pressure vessel walls, but since the cover acts as the support of the cooling device, the said device can be more simply and cheaply arranged, attached or formed on it.

By means of a still further development, a simple and robust structure is guaranteed while allowing the sample container to be introduced into or removed from the pressure vessel from above. The sample container stands on a preferably central and bar-shaped pedestal which makes possible the arrangement of the chamber for the medium underneath the sample container.

Other further developments according to the invention confer characteristics that contribute to solving the problem of simplifying the structure and making it more compact, so that the capacity of the pressure vessel can be enlarged, the number of components reduced, the function improved and made safer, and the structure is also less costly.

BRIEF DESCRIPTION OF THE DRAWINGS

In what follows, the invention and other advantages resulting from it will be explained in greater detail with reference to preferred embodiments and a number of 20 drawings, in which.

DETAILED DESCRIPTION OF THE PREFERRED EMBODIMENT

Figure 1:
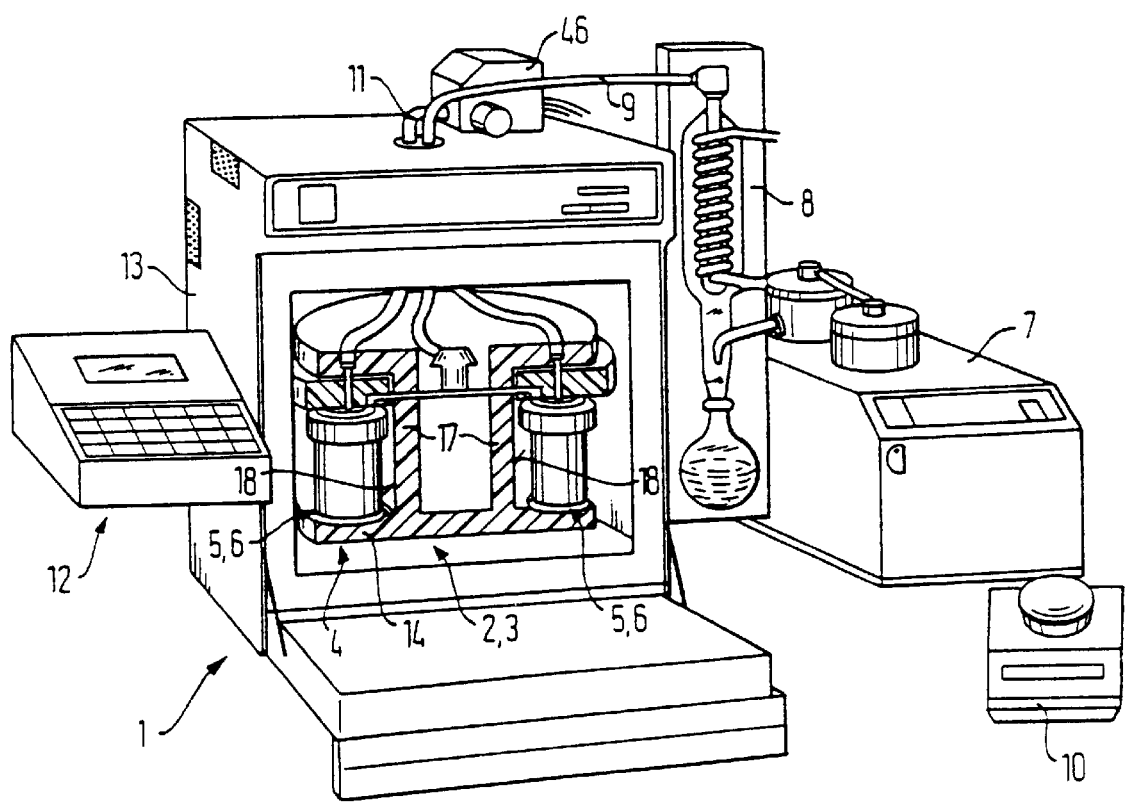
FIG. 1 is a simplified perspective view of a device according to the invention for the vaporization treatment of samples under reduced pressure in at least one container that can be opened or closed.

The main components of the device 1 are a heating device 2, preferably using microwaves, with a heating space 3 that can be closed, for example, by a door, a holder 4 arranged therein with several, preferably four or six stand positions 5 for containers 6, a suction pump 7, a condensation-cooler 8 fitted inside the suction pipe 9 leading to the suction pump 7, several inlet tubes 11 or a common manifold that branches into several inlet tubes for a solvent or a gas, for example air or an inert gas, and an electronic control device 12, preferably comprising a computer that operates with predetermined or input programs, the control device 12 preferably being associated with a keyboard and a display or VDU for the input of control data. In addition, the device 1 is associated with a weighing scale 10 inside or outside the heating space 3, preferably an electronic weighing scale 10, connected by an electric control lead to the control device 12. The latter may be integrated in the device itself, or arranged in the housing containing the keyboard and the VDU.

The heating apparatus 2 is integrated in a square-shaped housing 13, from the front of which the heating space 3 in the form of a square-shaped cavity, is accessible and closed off tightly by a shutter, in particular one that swivels upwards. The suction pipe 9 and inlet tubes 11 lead through associated openings into the heating space 3. The holder 4 consists of a material transparent to microwaves, in particular a plastic such as polypropylene, and is a rotating component with a lower turntable 14 and an upper turntable 15, between which the containers 6 are held. The rotating component can be driven in continuous rotation or in a back and forth oscillating movement, preferably through approximately 360°. The turntables 14, 15 are solidly attached to one another by a central, vertical connection piece, in this case a connection tube 17, so that they project outwards beyond the connection tube 17 and form between them a common annular space 18 or individual spaces to take the containers 6. As shown in particular by FIG. 2, the containers 6, all of the same form, each consist of a pot 23 and a flat cover 24, if necessary sealed by an interposed annular gasket. The covers 24 are each held under the upper turntable 15 in a vertically flexible way still to be described.

For preference, on the top of the lower turntable 14 and/or the underside of the cover 24 in the area of each stand position 5, a guideway 19 for the pot 23 is provided, to permit the radial inward movement of the pot 23 when it is introduced between the turntable 14 and the cover 24. The guideway 19 may be formed of a recess 21 with a flat bottom surface 21a, whose circumferential width is adapted to the width of the preferably cylindrical pot 23 and which forms an end-stop A for the radial inward movement of the pot 23.

The pot 23 of the container 6 consists of several, in the present case two parts, namely a lower part 26 and an upper part 27 fitting closely over its upper rim, at the center of which a space or chamber 28 opening upwards is provided for a sample holder 29. In the present design, the chamber 28 is formed by a vertical cylindrical hole whose bottom is formed by a conical surface 31 converging downwards at an inclination of around 45°. The chamber 28 is open at the bottom via a drain channel 32 extending downwards, preferably located centrally. The cross-sectional shape —size and depth of the chamber 28 —corresponds approximately to that of the size and height of the sample holder 29, so that the latter can be inserted from above into the chamber 28 with some freedom of movement. To be able to take the sample holder 29 out again, the chamber 28 has at its top one or more free spaces 33, for example enlargements of its cross-section, in the area of the upper rim of the preferably pot-shaped sample holder 29, which can be gripped by hand or, for example, with a pair of tongs.

In the present design, the sample holder 29 comprises a hollow cylindrical circumferential wall 29a and a preferably outwardly convex rounded bottom 29b, and consists of a material permeable to a liquid and transparent or partially absorbent to microwaves, in particular a filter material, preferably a fibrous glass or plastic material, designed approximately as a fleece pad and with a wall thickness of around 0.5 to 2 mm, especially about 1 mm. In its pot-shaped form, the sample holder 29 is strong or rigid enough to be gripped and handled, so that it can be held without being pressed flat. The diameter of the sample holder 29 is about 20 mm, and its height about 40 mm.

The chamber 28 is preferably formed of a thin-walled pot component 34, preferably integrally formed with the top part 27 of the pot. For this purpose, a flange-shaped radial wall 35 can be used, which rests on the rim of the lower part of the pot 26 and surrounds it in order to center it or engages with it via a projection, particularly an annular projection 36. To form a seal, between the wall 35 and the free rim 26a an annular gasket is provided, in this case an O-ring 37, which is seated in a circumferential groove of the annular projection 36 and forms a seal between the rim 26a and the wall 35. In the present design, the flange-shaped radial wall 35 with a hollow cylindrical wall portion 35a is preferably dome-shaped, with a flat, upwardly-facing support surface 35b for the cover 24 above the free rim 26a. By this means, different dome heights can be used not only to achieve adaptation between existing pot heights and cover heights, but the volume and height of the chamber 28 are also enlarged. For preference, on the underside of the cover 24 or the top side of the upper part of the pot 27, a lip seal is provided whose sealing lip 38 is formed in one piece on the cover 24 or preferably the upper part of the pot 27, and extends radially outwards with respect to the vertical central axis of the container 6 and is formed by a narrow circumferential groove 38a in the wall 35. The inside space of each container 6 is connected by suction channel branches 9a passing through the wall 35 and continuing radially inwards in the cover 24, to the common suction manifold 9 extending outwards and connected to the cooler 8 and suction pump 7. By uniting the suction manifold branches 9a, there is produced in that region a so-called rotary connection armature 39 known per se, at the center of the holder 4, from which the suction channel branches 9a extend preferably through sleeves 41 made of an elastic and flexible material, particularly plastic, fitted in corresponding holes of the associated cover 24 and a component 42 (connection pipe 17) of the holder 4 on the inside thereof for the armature 39.

In a comparable way, the common inlet manifold 11 extends into the heating space 3, and is preferably centrally connected by means of the inlet manifold branches 11a leading from it to the inner space of each container 6. Both for the suction manifold 9 and for the inlet manifold 11 or their branches, a rotary connection armature is needed when the holder 4 is rotated in the sense of a rotor by the drive motor not shown in the figure. When the motion is back and forth, connection hoses that allow this motion are sufficient.

Figure 2:
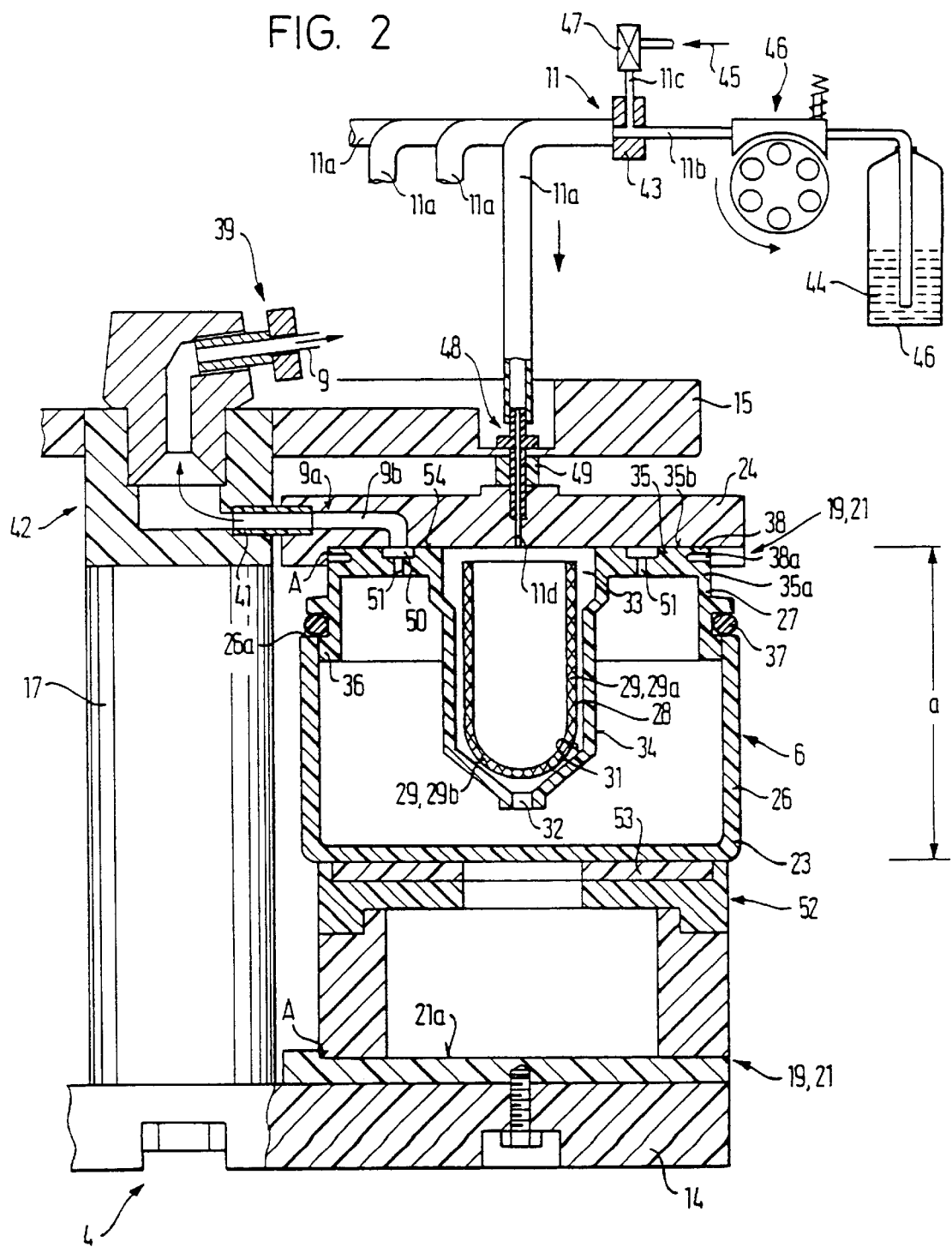
FIG. 2 is a partial vertical section of a holder arranged in the heating area of the device of FIG. 1 for one or more containers.

FIG. 2 shows the course of the inlet manifold 11 with the inlet pipe branches 11a branching off from one section 43 to the containers 6. The inlet manifold 11 or its branches 11a are used to introduce in particular a liquid reagent or solvent 44 and/or a flushing gas 45, for example air or an inert gas. For this, two further inlet pipe branches 11b, 11c are used, one of these branches 11b extending from a reservoir 46 for the solvent 44 via a pump 46, and the other branch 11c extending from a reservoir (not shown) for the flushing gas, preferably via an on-off and adjustable ventilation valve 47, to the inlet manifold 11. The inlet pipe branches 11a pass through the upper turntable 15 each in the area of a connection fitting 48, which can also serve as a holding element for the cover 24, arranged some distance below the upper turntable 15 and held on it in a vertically elastic flexible way. This is achieved by an elastic compression piece 49 arranged between the upper turntable 15 and the cover 24, which guarantees the vertical flexibility of the cover 24 which can be suspended on the upper turntable 15 by means of the connection fitting 48 passing through the compression piece 49 and into the cover 24. The mouths 11d of the branches 11a lead centrally into the inner space of the associated container.

On the top side of the upper part of the pot 27 there is a coaxial groove or annular recess 50, in whose area the associated suction pipe branch 9a opens into the cover 24 as an angular channel 9b. Within the annular groove 50 are several holes 51 passing through the wall 35 and arranged uniformly around its circumference, in this case four such holes, which guarantee uniform evacuation of the inner space of the container 6.

The pot components 26, 27 and if necessary also the cover 24 may consist of a material essentially transparent to microwaves such as plastic, glass, quartz or ceramic, or they may consist of a material which absorbs microwaves partially, so that during irradiation by the microwave generator (not shown) they are heated and thereby act as indirect heating elements or auxiliary heating elements to heat the sample material, or to avoid condensation especially in the upper part of the inner walls of the container. For preference, this material will be a plastic in which particles, especially particles of a microwave-absorbing material, preferably graphite, are mixed or incorporated. A plastic of this kind is known under the designation Weflon.

In the embodiment shown in FIG. 2, between the container 6 and the lower turntable 14 there is a pedestal 52 for the pot 23. On the top side of the pedestal 52, a plate 53 made of a material that partially absorbs microwaves can be placed, for the purpose of additional indirect heating from below. The lower part of the pot 26, with its preferably flat floor, preferably consists of a transparent material such as glass, quartz or plastic.

In the normal, released position of the cover 24, the vertical distance a between its lower or sealing surface 54 and the lower turntable 14 or the pedestal 52 is slightly smaller than the height of the pot 43. As a result, the cover 24 slightly compresses the compression piece 49 when it rests on the pot 23 after the latter has been pushed in from the side. When pushing the pot in or pulling it out from the side, the connections of the suction pipe branches 9a and inlet pipe branches 11a with the inner space of the associated container 6 are made (on insertion) or broken (on extraction) automatically. This makes for easy and rapid handling.

This device 1 is suitable for the drying and/or extraction of sample material previously introduced into the sample container 29. In both cases, during the operation of the device 1 the sample material is heated directly by the microwaves (if the sample material is a microwave absorber) and/or indirectly by the heating elements mentioned earlier, and because of the rotation or oscillation of the holder 4, this heating takes place uniformly. Vapors given off during the heating are extracted by the suction system from the containers 6, the vapors being flushed out completely by the flow of flushing gas 45. Because of the suction, the pressure in the containers 6 is reduced such that the boiling point of the liquids to be vaporized, for example water or moisture and/or the solvent 44, decreases and evaporation is forced and/or can take place at lower temperatures. In addition, the sealing function of the cover 24 is improved by the suction effect.

The device 1 is set up such that the flushing gas 45 and/or the solvent 44 can be admitted to treat the sample, this being adjustable by switching the pump 46 on or off or varying the pumping rate.

In the working area of an existing laboratory, the device 1 is associated with a further device 101, with which the sample material can be extracted under elevated pressure.

The main components of the device 101 are a heating device 102 preferably operating by microwaves, with a heating space 103 closed by a door 103a, a holder 104 positioned in the heating space 103 with several, preferably four or six stand positions 105 for pressure vessels 106, one overpressure valve 107 for each pressure vessel 106, which when a given inside container pressure (overpressure) is exceeded, opens automatically and then closes again under the action of an elastic compression piece, in each case with an adjustment device 108 for each valve 107 to preset its elastic prestress level, i.e. to regulate the internal pressure of the container at which the valve 107 opens automatically, and a cooling device 110 for each pressure vessel 106, that can be connected to a common supply of coolant 110a, for example a coolant pump 110b, in particular a water pump.

Figure 4:
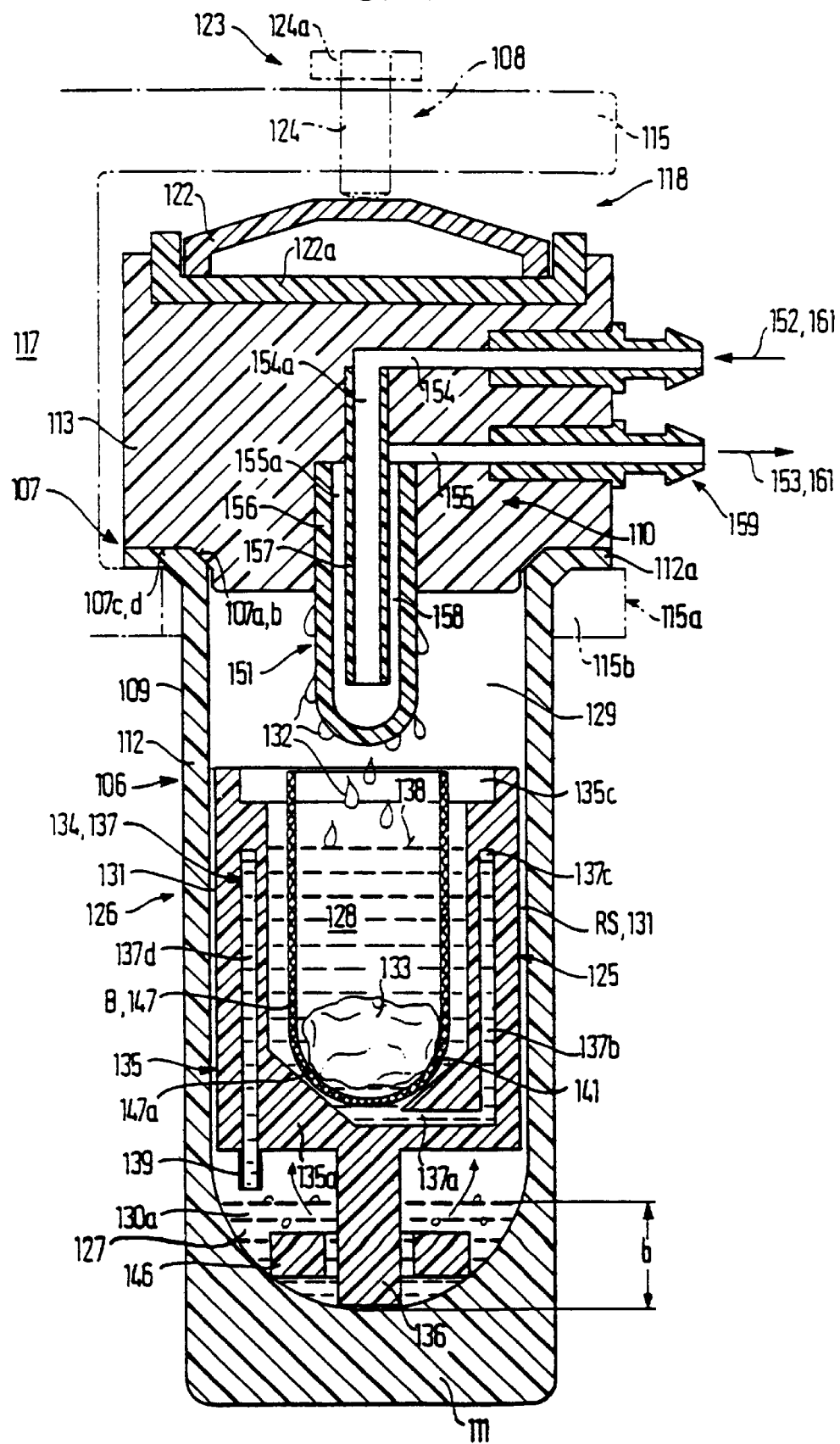
FIG. 4 is a partial vertical section through a holder for the containers arranged in the heating area of the device of FIG. 3, and through the containers therein.

As shown in FIG. 4, the pressure vessels 106 are all of similar design and consist of a pot-shaped housing 109 with a housing floor 111 and a hollow cylindrical, vertically extending housing wall 112. The aperture of the housing, which can be closed off by a cover 113, is limited by the upper inside rim of the housing wall 112 (FIG. 4).

The valve 107 is positioned in the upper area of the pressure vessel 106, its valve component preferably being formed by the cover 113. When a certain internal pressure in the pressure chamber 106 is exceeded, the valve 107 opens automatically, so that part of the internal pressure can escape to the outside. This prevents the internal pressure from exceeding a predetermined value that might overload the pressure vessel 106 or cause it to explode.

The valve seat of the valve 107 is formed at the upper inside rim of the hollow cylindrical housing wall 112, and is formed by a conical seating surface 107a concentric to the cylindrical housing wall 112 converging downwards, and/or a horizontal surface 107c. The cone angle is about 45° to about 75°, preferably approximately 60°. A correspondingly shaped conical sealing surface 107b and/or a horizontal sealing surface 107d is formed in the cover 113 that fits on the housing wall 112 from above.

As shown in FIG. 4, the holder 104 is a rotating component with a lower turntable 114 and an upper turntable 115, between which the pressure vessels 106 are held. The rotating component can be driven in continuous rotation or in a reciprocating movement, preferably around approximately 360°, to ensure uniform heating of the pressure vessels. The turntables 114, 115 are solidly connected together by a vertically extending connection piece, in this case a connection tube 117, such that they project radially outwards beyond the connection tube 117 and form a common annular space 118 or —when the holder 104 is a round block —individual, radially inwardly-directed spaces to receive the pressure vessels 106. For preference, on the upper side of the lower turntable 114 in the area of each stand position 105, a guideway 119 for the pressure vessel 106 is provided, which consists of a radially inwardly-extending movement guide with a movement end-stop A to facilitate insertion of the pressure vessel 106 from the side between the turntables 114, 115. The guideway 119 may be formed by a recess 121 with a flat bottom surface 121a, whose circumferential width is adapted to the width of the preferably cylindrical pressure vessel 106.

As shown in particular by FIG. 4, the adjustment device 108 associated with each of the stand positions 105 is formed by an adjustable clamping device 123, in particular a clamping screw 124, accessible from above and screwed into a threaded hole in the upper turntable 115. An elastic compression piece 122 is positioned between the pressure vessel 106 and the turntables 114, 115, preferably on the cover 113 and between the latter and the clamping screw 124. The compression piece 122 is preferably formed by a molded piece in the shape of a hollow cone, which may be positioned in an opening on top of the cover 113, or a compression disc 122a made of a high-strength material, in particular plastic. The clamping screw 124 is at its upper end provided with a gripping element 124a for a turning tool. By setting the clamping screw 124 to a corresponding position, the valve 107 can be so adjusted that it will open and allow the escape of pressure from inside the pressure vessel at any desired value.

Within the scope of the invention it is also possible to position the pressure vessel or vessels not standing, but suspended between the turntables 114, 115, for which purpose a peripheral flange 112a of each pot-shaped housing 109 is held by a lower turntable 115a with a corresponding radial insertion opening 115b, as illustrated in FIG. 4. With a suspended arrangement of this type, the bottom of the housing 111 may be rounded not only on the inside but also outside, in particular forming a hemisphere, whereby less material is needed.

Figure 3:
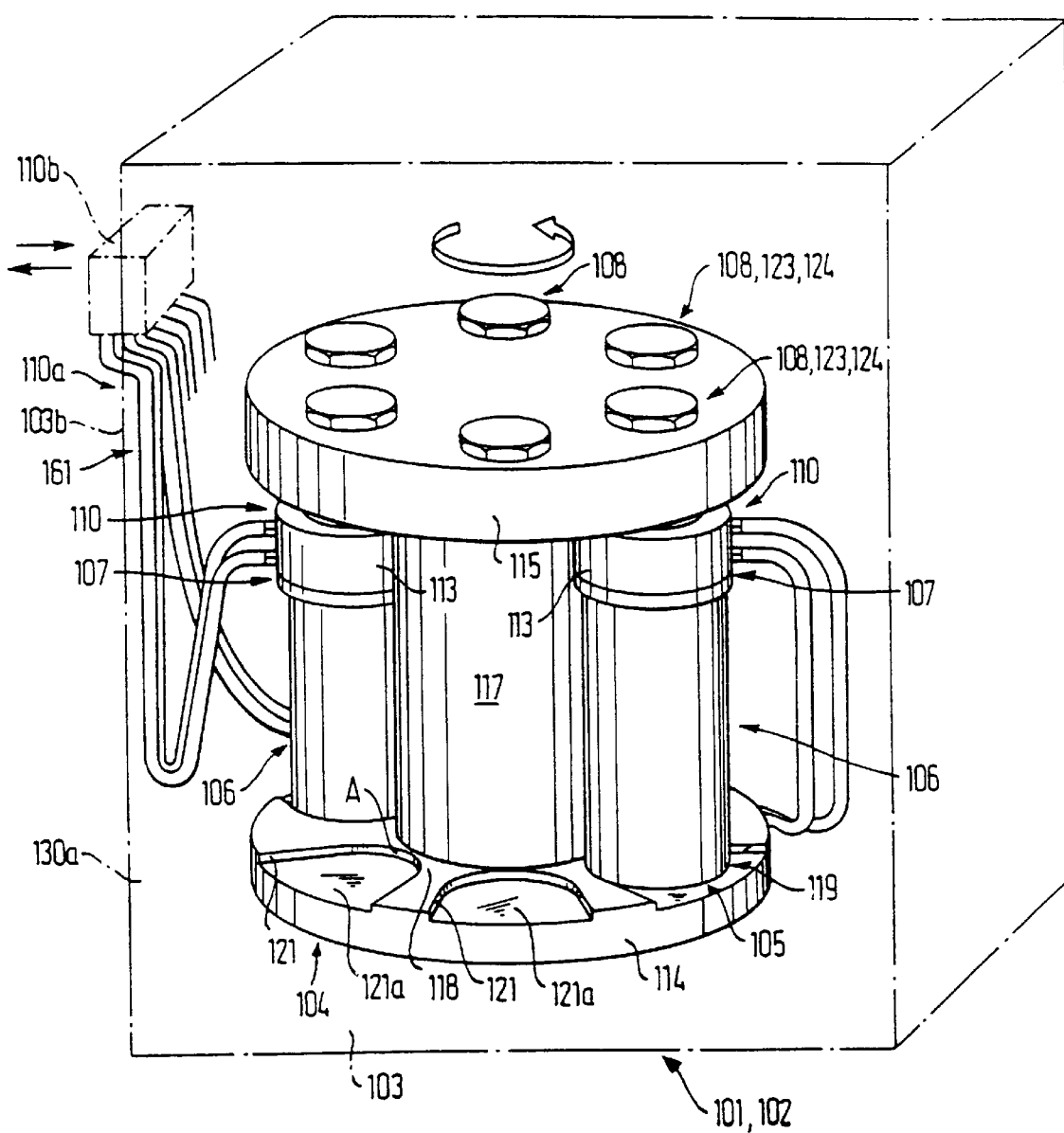
FIG. 3 is a simplified perspective front view of a device according to the invention for the extraction of samples in at least one container by means of a solvent at elevated temperature and elevated pressure.

In the standing arrangement of the pressure vessel 106 shown in FIGS. 3 and 4 by continuous lines, the housing floor 111 is rounded to form a hemisphere on the inside and is flat or horizontal on the outside, which requires the use of somewhat more material.

The pressure vessels 106 are of similar design. In each pressure vessel 106, an extractor 125 and a so-termed Soxhlet apparatus 126 is integrated, as shown.

In greater detail, in the pressure vessel 106 a solvent chamber 127 and over it a sample chamber 128 are arranged, with a vapor duct extending upwards between the solvent chamber 127 and a vapor space 129 above the sample chamber 128, with a cooling device 110 so arranged in the vapor space 129 that any condensate 132 of the reagent or solvent produced in the area of the cooling device 110 will run down into the sample chamber 128 and preferably drop on to the sample 133 therein, and with the sample chamber 128 associated with an overflow 134 leading to the solvent chamber 127.

In the present preferred design, the sample chamber 128 is arranged in a sample holder 135 of pot-shaped form made as a separate component, which can be inserted from the top into the housing 109 and is supported above the solvent chamber 127 to prevent it descending too far down into the solvent chamber 127. For preference, this is achieved in particular by a central support bar 136 in the form of a narrow extension of the sample container 135 reaching from its container bottom downwards to the bottom 111 of the housing. The sample container 135 has an outer diameter somewhat smaller than the inner diameter of the housing 9, so that between them there is an annular space RS forming the vapor duct 131. The overflow 134 is integrated into the body of the sample container 135, i.e. it forms channels passing through the latter, so that no parts of the overflow channel 137 project radially outwards. More precisely, the overflow channel 137 consists of a channel section 137a extending radially outwards from the bottom area of the sample chamber 128, from which a second channel section 137b extends upwards to the level 138 of the sample container 135, a horizontal channel section 137c preferably extending in the circumferential direction, and a vertical channel section 137d, with the horizontal channel section 137c, and channel sections 137a and 137d connected together and channel section 137d opening downwards from the body of the sample container 135 preferably in the form of a tube section 139 extending into the sample container from underneath. The height of the solvent chamber 127 is greater than the level b of the solvent 130a, so that the vapor can flow away freely.

For preference, the sample container 135 consists of several individual components enabling the channel sections 137a to 137d to be produced by injection molding, so that no machining need be done and material can therefore be used sparingly such as to reduce production costs.

The bottom 135a of the sample container 135 is preferably formed convergently downwards, particularly in the shape of a hollow cone.

The sample container 135 or its individual components and/or the housing 109 can essentially consist of a material transparent to microwaves, in particular plastic, glass, quartz or porcelain, or of a material which absorbs microwaves in part, for which purpose a material transparent to microwaves, in particular plastic, in which particles of a material that absorbs microwaves are embedded, may be used. A preferred material is plastic in which particles of a microwave-absorbing material, in particular graphite, are mixed or incorporated, which is known under the designation Weflon.

A microwave-transparent material for the sample holder 135 is suitable in cases when the solvent and/or the sample material are substances that absorb microwaves, and that will thus be directly heated by the microwave radiation. If a microwave-transparent material is used as the solvent and/or sample material, an indirect heating body is needed for the heating of the sample 133 and/or the solvent, which in the present case is formed by the sample container 135 itself which produces the necessary heat and transfers it to the solvent 130 and the sample 133 in the sample container 135 and to the solvent 130a present in the solvent chamber 127. The heating of the solvent 130a in the solvent chamber 127 is important, to contribute to its vaporization, as will be described below. To enhance the heating of the solvent 130a, at least one further component made of a microwave-absorbing material, preferably also Weflon, may be positioned in the solvent chamber 127. In the present design, at least one component, in particular a ring 146, is provided in the solvent chamber 127 to act as an additional indirect heating body, through which the support bar 136 passes.

To facilitate the insertion and removal of the sample 133, a sieve-shaped sample holder 147 in the form of a pot to take the sample 133 is provided, which can be inserted from above into the sample container 135. For preference, the bottom of the sieve 147a is rounded or hemispherical, so that the sample 133 will lie in the hollow of the sample holder 147 standing on the bottom 135a, in which the sample will be moistened even with the residual quantity of the solvent 130 present. The sample holder 147 is preferably of a size such that it projects beyond the sample container 135 or up into the area of the space over the closure ring 135c, where it can easily be gripped from above. The sample holder 147 consists in particular of plastic, glass or quartz, preferably a fibre material, and may comprise the microwave-absorbing material already described.

It is advantageous to make at least one of the pressure vessels 106, preferably several or all of them, and at least one sample container 135, out of a microwave-transparent material and one sample container 135 out of a microwave-absorbent material, so that depending on the application, the material of the solvent 130 and/or the sample 133, the most appropriate container 135 from the-standpoint of temperature development can be used interchangeably.

For preference, the cooling device 110 possesses a cooling body 151 arranged at the center of the underside of the cover 113, particularly in the form of a cooling rod or finger, and which is either convergent at its lower end or of a cross-section only so large as to allow any condensate formed on it to run down into the sample container 135 and in particular on to the sample 133. In the present design, a cylindrical cooling body 151 is provided, whose lower end tapers downwards, and in particular, is hemispherical. The cooling body 151 is connected to a coolant circuit whose coolant may be air or preferably a liquid, for example water. The cooling body 151 is attached to the cover 113. It is therefore advantageous to connect the inlet and outlet pipes 152, 153 for the coolant sideways to the cover 113, such that they pass through adjacent horizontal channels 154, 155 in the cover 113 and extend as far as the cooling body 151. The vertical channel sections 154a, 155a passing through the cooling body 151 are preferably coaxial, such that the cooling body 151 has a hollow cylindrical wall 156 into which a tube section 157 extends coaxially from above, and whose lower end terminates shortly above the bottom wall of the cooling body 151 and to whose upper end the inlet tube 152 is connected, while the outlet tube 153 leads away from the upper end region of the annular space 158 between the hollow cylindrical wall 156 and the tube section 157.

Around the periphery of the cover 113 there are plug couplings 159, in particular rapid connection joints, for the connection of hoses 161 shown only in FIG. 3, which preferably pass through the housing wall 103b of the heating device 102 and are connected to the external pump 110b.

All other parts of the pressure vessel 106 including the oscillating holder 104 and the hoses 161 are made of materials transparent to microwaves.

The device 101 operates as follows:

To prepare or extract the sample material in at least one pressure vessel 106 of the device 101, solvent 130 and/or 130a is introduced into the pressure vessel 106 that has been removed from the holder 104 and opened, and the associated sample 133 is placed in the housing 112 or sample container 135. The housing 109 is then closed by the cover 113 and the pressure vessel 106 is replaced in the holder 104 and clamped in it, and the connections 161 of the cooling device 110 are established. When the heating space 103 has been closed, the microwave generator is switched on and for preference, the holder 104 is set into rotation. During the microwave irradiation, the solvent and sample material (sample 133), depending on the material, are heated directly or indirectly by the components (sample holder 135, ring 146) acting as heating bodies, so increasing both the inside temperature in the pressure vessel 106, and the inside pressure as a result of the heating and evaporation of the solvent 130. The vapor rises up from the solvent chamber 127 through the annular gap RS between the sample container 135 and the housing wall 112 (vapor duct 131), or through one or more grooves in the circumferential surface, given that it is prevented from cooling by heat transfer from the sample container 135. In the vapor space 129, the vapor precipitates on the cooling body 151 as a condensate and drops into the sample chamber 128 and onto the sample 133. When the condensed solvent 130b reaches the level 138 therein, no further rise is possible since the solvent 130b flows back through the overflow 134 into the solvent chamber 127. This is possible owing to the suction effect of the outlet (137d, 139) leading into the solvent chamber 127. In this way, the solvent 130 and 130a can be used in a continuous cycle, until a given level of saturation has been reached.

In this device 101 and process, extraction takes place in a closed system, and not only under excess pressure but also at an elevated extraction temperature. This results in improved solubility.

In what follows, further advantages of the device 101 or the process carried out with it will be described.

There is an automatic cycle of the solvent, in which thanks to the elevated pressure and boiling point, better wetting and extraction of the sample material is achieved, since the solvent is forced into the sample material by the pressure. For example, the boiling point of dichloromethane increases from 57° C. at normal pressure to 51° C. at about 10 bar.

Owing to the closed cycle of the solvent, the consumption of solvent is lower, and losses by evaporation outside the system do not take place.

Thanks to the selective heat input (microwave absorption by the solvent or synthetic and inert heating elements), the heating time is also short.

Vapors released when the pressure chamber is opened can easily be drawn off, for example by a suction device connected to the heating space, which avoids vapor concentrations in the workshop. This is particularly important in the case of toxic solvents.

It is therefore evident that the device 1 and the device 101 can be advantageously used for the vaporization or drying and extraction of samples, the device 101 being particularly suitable for extraction.

However, within the scope of the invention it is also possible and advantageous to use both devices 1, 101 for an extraction process, especially when the sample holders 29, 147 and the chambers 28, 162 receiving them are of essentially similar shape and size, so that a single sample holder B can be used as the sample holder common to both devices 1, 101. In such a case, the sample in its sample holder B can be used and treated in both devices.

Below, an example of such a process for the extraction and drying of a sample will be described. The sample, for example cheese, is introduced into the sample holder B and weighed. The sample holder B is then placed in the holding chamber 28 of a container 6, and the latter is pressed into the holder 4. A drying process is then carried out in device 1 by heating with microwaves as described above, during which the vapors are extracted and an underpressure produced thereby, which accelerates the drying.

As the next step, for example, the fat content of the dry mass is established by dissolving out the fat. For this extraction, the sample holder B with its sample material is removed from the container 6, inserted into the chamber 162 of a pressure vessel 106 of the device 101 with the housing 109 open, the pressure vessel 106 is closed and inserted into the holder 104 of the device 101, and the latter is set into operation, whereby the sample is heated as described above and extracted under excess pressure and at an elevated temperature. Suitable solvents are, for example, hydrocarbons.

At the end of this extraction step, the sample holder B with the extracted sample material is removed from the pressure vessel 106 once the latter has been taken out of the device 101 and opened, and with the pump 46 turned off or disconnected, i.e. without any input of solvent 44, dried once more to remove solvents from the sample residue. At the end of the new drying process, the sample holder B with the extracted and dried sample residue is removed and weighed again, to establish the fat content.

Any transport of a sample between various treatment steps in various containers or devices involves the risk of contamination or loss of parts of the sample, and necessarily leads to errors. This disadvantage is avoided by the process according to the invention, since one and the same sample container B is used in both devices 1 and 101.

I claim:
1. A process for the extraction of samples by means of a volatile solvent, said process comprising the steps of:
   placing the sample in a sample holder in a container of a first device,
   heating the sample and the volatile solvent,
   whereby extraction takes place in the closed container under elevated pressure,
   wherein said process includes the steps of:
      transferring the sample with its sample holder into a second device, said second device comprising a container into which the sample holder also fits,
      drying the sample in the container of the second device, and
      drawing off the vapors so produced,
      whereby there is produced an underpressure in the container of the second device.
2. A process according to claim 1, wherein,
   before causing extraction in the first device, drying the sample by heating it in the container of the second device,
   drawing off the vapors so produced, and
   thereby producing an underpressure in the second container.
3. Apparatus for carrying out a process according to claim 1 or 2, said apparatus comprising,
   a first device which includes,
   at least one container,
   a microwave heater having a container holder for holding the container in a heating space,
   a receptacle chamber within the container for a volatile medium,
   said container having a sample holder for holding the sample in said receptacle chamber,
   wherein
      the first device is associated with a second device for the evaporation and drying of the sample in at least one second device container,
      in that the second device comprises a heating chamber that is heated by microwaves, a suction device with a suction manifold and an inlet device with an inlet manifold for a gas,
      in that the suction manifold and the inlet manifold are connected to the inside space of the second device container,
      and in that the containers of the first and second devices are so designed that the same sample holder can fit into both of them.
4. Apparatus according to claim 3 wherein
   the first device comprises at least one pressure vessel including
      a first chamber to receive the volatile solvent,
      a sample container positioned higher than the first chamber, and having a second chamber to receive a sample, at least one heating element of microwave-absorbent material to heat the volatile solvent, and the heating element being positioned in at least one of the first and second chambers.

5. Apparatus according to claim 3 wherein the first device comprises at least one pressure vessel including a first chamber to receive the volatile solvent, a sample container positioned higher than the first chamber, and having a second chamber to receive a sample, at least one heating element of microwave-absorbent material to heat the volatile solvent, and the heating element forming the second chamber.

6. Apparatus according to claim 3 wherein the first device comprises at least one pressure vessel including, a first chamber to receive the volatile solvent and a sample container positioned higher than the first chamber, and having a second chamber to receive a sample, said first device including a closeable heating space to receive the pressure vessel, said pressure vessel comprising a pot-shaped housing with a cover made of a microwave-transparent material that rests freely on the housing, said pressure vessel also forming the first chamber, and the inner surface of the bottom of the pressure vessel being rounded to form a hemisphere.

7. Apparatus according to claim 3, wherein the first device comprises at least one pressure vessel including a first chamber to receive the volatile solvent, a sample container positioned higher than the first chamber and having a second chamber to receive a sample, a vapor duct connecting the first chamber with the second chamber, an overflow duct connecting the second chamber with the first chamber, and a cooling device for a vapor space positioned over the sample container, and in that the sample container comprises a pedestal which projects into the first chamber, and in that at least one of the sample container and the pedestal is comprised at least in part of one of a microwave-transparent and a microwave-absorbing material.

8. Apparatus according to claim 3, wherein the first device comprises at least one pressure vessel including a first chamber to receive the volatile solvent, a sample container positioned higher than the first chamber and having a second chamber to receive a sample, a vapor duct connecting the first chamber with the second chamber, an overflow duct connecting the second chamber with the first chamber, and a cooling device for a vapor space positioned over the sample container, and in that the sample container comprises a pedestal which stands on the bottom of the first chamber, and in that at least one of the sample container and the pedestal is comprised at least in part of one of a microwave-transparent and a microwave-absorbing material.

9. A device for the extraction of components from samples by means of a volatile solvent, in at least one pressure vessel, said device comprising:

a pressure vessel which includes:

a first chamber for receiving the volatile solvent, a sample container higher than the first chamber with a second chamber for receiving a sample, and at least one heating element of microwave absorbent material provided in the pressure vessel, wherein, the heating element is positioned within at least one of the first and second chambers.

10. A device according to claim 9 wherein the heating element is formed by a pedestal of the sample container wherein the pedestal consists of a microwave-absorbing material and projects into the first chamber.

11. A device according to claim 10, wherein, said pedestal stands on the bottom of said first chamber.

12. A device according to claim 9, wherein, at least one of the heating element and the sample container consists at least in part of plastic.

13. A device according to claim 9, wherein, said heating element consists at least in part of plastic.

14. A device according to claim 10, wherein, at least one of the sample container and the pedestal consists at least in part of plastic.

15. A device according to any of claims 9, 10, 11, 12, 13, or 14, wherein, the sample container consists of a microwave-absorbent material.

16. A device according to any of claims 10, 11, 13 or 14, wherein, the pedestal is formed by a bar projecting downwards.

17. A device according to claim 15, wherein, the pedestal is formed by a bar projecting downwards.

18. A device according to any of claims 10, 11, 12, or 13, wherein, the heating element is formed by a ring.

19. A device according to claim 16, wherein, the heating element is formed by a ring and in that the ring encircles the bar.

20. A device according to claim 17, wherein, the heating element is formed by a ring and in that the ring encircles the bar.

21. A device according to any of claims 10, 11, 13 and 14, wherein, the pedestal is formed by a bar projecting downward and in that the heating element is formed by a ring which encircles the bar.

22. A device according to claim 19, wherein, the sample container consists of a microwave-absorbent material.

23. A device according to claim 20, wherein, the sample container consists of a microwave-absorbent material.

24. A device according to claim 21, wherein, the sample container consists of a microwave-absorbent material.

25. A device according to any of claims 9, 10, 11, 12, 13 or 14, wherein, that the chamber to receive the volatile solvent is positioned in the bottom area of the pressure vessel.

26. A device according to claim 10, wherein,
the sample container consists of a microwave-absorbent material.
27. A device according to claim 10, wherein,
the pedestal is formed by a bar projecting downwards.
28. A device according to claim 27, wherein,
the heating device is formed by a ring.
29. The device according to claim 27 wherein the heating element in the first chamber is a ring.
30. A device according to claim 10, wherein,
the pedestal is formed by a bar projecting downward and in that the heating element is formed by a ring which encircles the bar.

* * * * *